United States Patent
Doerr et al.

(10) Patent No.: US 9,220,914 B2
(45) Date of Patent: Dec. 29, 2015

(54) MAINTENANCE SYSTEM FOR MAINTAINING AN ENERGY ACCUMULATOR ARRANGEMENT

(75) Inventors: Thomas Doerr, Berlin (DE); Volker Lang, West Linn, OR (US)

(73) Assignee: BIOTRONIK SE & CO KG (DE)

(*) Notice: Subject to any disclaimer, the term of this patent is extended or adjusted under 35 U.S.C. 154(b) by 969 days.

(21) Appl. No.: 13/084,624

(22) Filed: Apr. 12, 2011

(65) Prior Publication Data
US 2011/0270337 A1    Nov. 3, 2011

Related U.S. Application Data

(60) Provisional application No. 61/329,102, filed on Apr. 29, 2010.

(51) Int. Cl.
*A61N 1/37*    (2006.01)
*A61N 1/39*    (2006.01)
*A61N 1/378*   (2006.01)

(52) U.S. Cl.
CPC .......... *A61N 1/3975* (2013.01); *A61N 1/3937* (2013.01); *A61N 1/3708* (2013.01); *A61N 1/378* (2013.01); *Y02B 60/50* (2013.01)

(58) Field of Classification Search
CPC ... A61N 1/3975; A61N 1/3708; A61N 1/378; A61N 1/3937
USPC ...................... 607/5, 29–33, 60–61
See application file for complete search history.

(56) References Cited

U.S. PATENT DOCUMENTS

| | | |
|---|---|---|
| 4,686,990 A | 8/1987 | Moberg |
| 4,715,381 A | 12/1987 | Moberg |
| 5,522,851 A | 6/1996 | Fayram |
| 5,741,307 A | 4/1998 | Kroll |
| 5,801,917 A | 9/1998 | Elias |
| 5,814,082 A | 9/1998 | Fayram et al. |
| 5,899,923 A | 5/1999 | Kroll et al. |

(Continued)

FOREIGN PATENT DOCUMENTS

WO    WO 2006/122198 A2    11/2006

OTHER PUBLICATIONS

European Search Report, 11161560.5-2305, Jun. 7, 2011.

*Primary Examiner* — Michael Kahelin
*Assistant Examiner* — Minh Duc Pham
(74) *Attorney, Agent, or Firm* — Craig A. Fieschko, Esq.; DeWitt Ross & Stevens S.C.

(57) ABSTRACT

An energy accumulator arrangement for an electromedical implant includes a battery, a capacitor, and a charging device which is designed to supply an electric charge from the battery to the capacitor according to a charging program. A maintenance system for maintaining the energy accumulator arrangement includes a monitoring device contained in the implant which captures a physical parameter value of the energy accumulator arrangement; an evaluation unit for evaluating the captured physical parameter value and generating a resulting evaluation result signal; a transceiver contained in the implant which sends the captured physical parameter value to the evaluation unit, and receive the evaluation result signal generated by the evaluation unit; and additionally a control unit contained in the implant which controls the charging device and the monitoring device, and adapts the charging program as a function of the evaluation result signal.

17 Claims, 10 Drawing Sheets

(56) References Cited

U.S. PATENT DOCUMENTS

| | | |
|---|---|---|
| 5,925,068 A | 7/1999 | Kroll |
| 5,983,472 A | 11/1999 | Fayram et al. |
| 6,096,062 A * | 8/2000 | Silvian .............................. 607/5 |
| 6,108,579 A | 8/2000 | Snell et al. |
| 6,115,633 A | 9/2000 | Lang et al. |
| 6,477,412 B1 | 11/2002 | Youker et al. |
| 6,826,427 B1 | 11/2004 | Fayram et al. |
| 6,906,605 B2 | 6/2005 | Lang |
| 7,181,270 B2 | 2/2007 | Breithardt et al. |
| 7,197,360 B1 | 3/2007 | Moulder et al. |
| 7,324,849 B1 | 1/2008 | Fayram et al. |
| 7,640,058 B2 | 12/2009 | Lang |
| 7,676,272 B2 | 3/2010 | Lang |
| 7,769,453 B2 | 8/2010 | Doerr et al. |
| 7,890,160 B2 | 2/2011 | Lang |
| 7,899,520 B2 | 3/2011 | Lian et al. |
| 2003/0191504 A1* | 10/2003 | Meadows et al. ............... 607/33 |
| 2005/0165456 A1* | 7/2005 | Mann et al. ..................... 607/30 |
| 2006/0259082 A1* | 11/2006 | Youker et al. ..................... 607/7 |
| 2009/0030487 A1* | 1/2009 | Lang .............................. 607/60 |
| 2010/0114216 A1* | 5/2010 | Krause et al. ..................... 607/5 |

* cited by examiner

MAINTENANCE SYSTEM FOR MAINTAINING AN ENERGY ACCUMULATOR ARRANGEMENT

CROSS-REFERENCE TO RELATED APPLICATIONS

This application claims priority under 35 USC §119(e) to U.S. Provisional Patent Application 61/329,102 filed 29 Apr. 2010, the entirety of which is incorporated by reference herein.

FIELD OF THE INVENTION

The present invention relates to a maintenance system for maintaining an energy accumulator arrangement of an implant.

BACKGROUND OF THE INVENTION

Energy accumulator arrangements for implants are known, wherein such arrangements include a battery, a capacitor, and a charging device, wherein the charging device is designed to supply an electric charge from the battery to the capacitor in accordance with a charging program. Such devices are also referred to as devices for battery and/or capacitor reformation. Contrary to the simple charging of the capacitor or battery, reforming denotes a controlled charging of the capacitor or battery, where the charging is carried out according to a charging program. Reforming a capacitor instead of uncontrolled charging is necessary in order to achieve as long a service life of the capacitor as possible.

On an electrolyte capacitor, which is used frequently in implants, a very thin oxide layer is provided on the positive electrode as an insulator between the two electrodes. A small leakage current is required between the two electrodes in order to maintain this insulating oxide layer. When this leakage current is absent, for example because the capacitor has not been charged for an extended period of time, the oxide layer substantially loses its insulating effect. As a result, very high currents may develop during the uncontrolled charging of the capacitor, which apply high loads on the capacitor and may irreversibly destroy it.

In order to achieve a long service life, capacitors of implants are therefore charged (reformed) in accordance with a charging program, which is generally designed such that a small charging current is applied to the capacitor, allowing the oxide layer to reform and regain its insulating properties. Such a reformation may take several seconds to hours and is carried out periodically (every 30 days, for example).

Methods for the controlled charging of a capacitor for an implantable device are known, for example, from U.S. Pat. No. 6,096,062. In this method, the high voltage capacitor is charged to an initial voltage which is lower than the peak voltage of the capacitor. Thereafter, a leakage current is measured. If the leakage current drops below a predetermined threshold value, the high voltage capacitor is not charged further. On the other hand, if the leakage current exceeds the predetermined threshold value, the high voltage capacitor continues to be charged up to the peak voltage and the peak voltage is maintained, allowing the high voltage capacitor to be reformed.

The problem with known maintenance systems is that the batteries and capacitors of the implants continue to have a comparatively short service life.

SUMMARY OF THE INVENTION

The invention proposes a maintenance system for maintaining an energy accumulator arrangement of an implant, by which the service life of the energy accumulator arrangement can be increased.

In a preferred version of the invention, the maintenance system includes:
- a monitoring device which is contained in the implant, and which is configured to capture and provide a value of a physical parameter of the energy accumulator arrangement;
- an evaluation unit for evaluating the captured value of the physical parameter, wherein the evaluation unit is configured to generate an evaluation result signal as a function of the captured value;
- a transceiver which is contained in the implant, and which is configured to send the captured value of the physical parameter to the evaluation unit, and to receive and send the evaluation result signal generated by the evaluation; and
- a control unit which can be implanted with the implant for controlling the charging device and the monitoring device, and which is configured to adapt the charging program as a function of the evaluation result signal.

The invention incorporates the realization that parameters for reformation of batteries and capacitors of an implant, such as a reformation interval, a charging voltage, a charging current, or a reformation duration, have so far been very difficult to adapt to the changing requirements in the implanted state of the implant. A particular problem is that the parameters for reformation in a new generation or version of a device are generally only is defined within a rough tolerance range, and are not adapted to the actual properties of the battery or capacitor. Under these circumstances, the reformation of the capacitor is carried out very inefficiently. Further, when the properties of the capacitor or battery vary drastically from the target properties, these roughly determined reformation parameters may result in damage and possibly irreversible destruction of the components. This occurs, for example, when a capacitor, which has excessive leakage current, is charged to the rated voltage thereof as part of a regular reformation process. Instead of healing the oxide defect as intended, the result may be thermal destruction of the capacitor. In known maintenance systems, reformation of the capacitor is also carried out even if the voltage of the battery is too low to do so.

If the roughly designed parameters for reforming the capacitor or battery are outwardly apparent, in known maintenance systems the options for revising the dimensioning of the parameters for reformation are drastically limited or even non-existent. In general, the patient wearing the implant must be scheduled for a visit to a doctor or other skilled personnel, with the consequence that rapid and convenient revision of the reformation parameters is not possible.

The invention further recognizes that capacitor reformation is carried out prophylactically in many known maintenance system, in other words, reformation is carried out even though there may not necessarily be an acute need for capacitor reformation. This can result in a significant reduction of the service life of an implant, in particular of an ICD (implantable cardioverter/defibrillator). A capacitor of the implant is charged, for example, every three months to the full rated voltage. In general, the charging time is estimated, and if the rated voltage is not reached within the specified charging time, the charging process is aborted. As a result, developing capacitor problems, such as too high a leakage current, cannot be detected in a timely fashion, and the capacitor, as described above, may be effectively destroyed by the prophylactic reformation. In known maintenance systems, a capacitor problem is usually only noticed when the implant experiences premature failure.

The maintenance system has the advantage that a developing battery and/or capacitor problem in the implant, which is manifested by a certain value of the physical parameter, can be treated promptly with the help of the monitoring device, the evaluation unit, and the control unit by continuously and automatically adapting the charging program. In this way, the maintenance system achieves a longer implant service, improved operating reliability, and more efficient operation of the energy accumulator arrangement. In particular, the maintenance system prevents premature device failures.

In addition, the maintenance system allows the charging program—and therefore the parameters for reformation—to be adapted as needed to the requirements of the particular battery or the particular capacitor. No patient visit has to be scheduled in order to adapt the charging program. The charging program adapted by the control unit is configured such the charging of the capacitor in accordance with the adapted charging program, i.e., the reformation of the capacitor, does not cause any damage to the capacitor or battery.

The maintenance system enables the individual observation of several energy accumulator arrangements of implants in use, as well as the fast and continuous adaptation of their charging programs, without the need to schedule visits for the patients wearing the implants. By using an adapted charging program, the charging devices charge the capacitors when an actual need for reforming exists. This eliminates prophylactic reformation, whereby energy savings can be achieved and the risk of damaging the energy accumulator arrangement is reduced.

In addition, adapting the charging program enables efficient, that is low-loss, charging of the capacitor. The charging program is adapted, for example, by changing the reformation interval between battery and/or capacitor reformations; by changing the duration of the reformation; by changing a charging voltage or a charging current; and/or by changing the number of capacitors to be charged. In general, the capacitor of the implant includes several individual capacitors connected in parallel or in series.

The monitoring device contained in the implant can capture a certain charging time, a value of a charging voltage, a charging voltage, a value of a charging current, a value of a charge state, and/or a value of another physical parameter of the energy accumulator arrangement, and provide the captured value(s) of the physical parameter(s) to the evaluation unit. The evaluation unit for evaluating the captured value may be located within or outside of the implant, and can evaluate the value of the physical parameter and provide a corresponding evaluation result signal.

The control unit contained in the implant for controlling the charging device and the monitoring device communicates with the evaluation unit by way of a transceiver, which is likewise contained in the implant. The monitoring device transmits the value of the captured physical parameter to the evaluation unit using the transceiver. The evaluation unit, which can also be equipped with a transceiver, can transmit the evaluation result signal to the control unit using the transceiver. The control unit adapts the charging program on the basis of the result signal that is received.

The evaluation result signal can contain target reformation parameters, and the control unit can adapt the charging program, i.e, the control unit controls the charging device in accordance with the received target reformation parameters. The evaluation is therefore preferably designed to generate and provide an evaluation result signal in the form of target reformation parameters.

Because the control unit is configured to control the charging device and the monitoring device, the physical parameter can be captured in a manner that is coordinated with the charging process of the capacitor in terms of time.

Additional advantageous versions of the maintenance system will now be described. The characteristics of these versions can be combined with each other and/or with the optional characteristics of the maintenance system mentioned above to form new exemplary versions.

The capacitor is preferably an electrolyte capacitor, for example, and the battery is preferably a silver vanadium oxide battery, for example.

In a particularly preferred version of the maintenance system, the evaluation unit is configured to receive several values of the physical parameter(s) of energy accumulator arrangements of several different implants, and to generate the evaluation result signal as part of an overall evaluation of the several values. In this version of the maintenance system, the evaluation unit therefore receives the several values of the physical parameter(s) from several different implants. The different implants (which are worn by different persons) preferably include energy accumulator arrangements which, in each case, are identical in design. In this version of the maintenance system, the evaluation unit is preferably located outside of the implant and transmits the evaluation result signal to at least one of the several different implants. For this purpose, the evaluation unit is operatively connected to the implants by way of a data network or network-based communications, e.g., via the internet or another communications network.

Through the overall evaluation of the several values, a superior evaluation result signal can be generated. The overall evaluation may include, for example, statistical assessments and averaging, or other mathematical methods for evaluating the several values and for generating the evaluation result signal. The advantage of this version is, in particular, that the evaluation result signal is generated not only as a function of one value of the physical parameter, but as a function of the several values of the physical parameter of energy accumulator arrangements which preferably have identical designs. In this way, the advantages of the maintenance system described above can be achieved not only for a single implant, but for several implants implanted in different persons.

For this purpose, the evaluation unit is preferably operatively connected to the monitoring device and the control unit by way of a patient device and the transceiver. In this way, the transceiver can be operated at low power, because it only ensures data transfer between the patient device, which is generally located in the vicinity of the patient (e.g., as a unit based in the patient's home), and the implant.

In this way, overall comprehensive adaptation of the charging program, i.e., a comprehensive change of the reformation pattern, is possible for several patients without scheduling visits.

In a preferred version, the control unit of the maintenance system is configured to adapt the charging program as a function of the evaluation result signal by changing one or more of a charging voltage, charging intervals, and a charging current. Such an adaptation of the charging program can increase the service life of the energy accumulator arrangement, and therefore the service life of the implant.

In a further particularly preferred version of the maintenance system, the evaluation unit is configured to access a database including manufacturing data characterizing the particular implant type in order to generate the evaluation result signal. In this version, the evaluation unit is preferably located outside of the implant and communicates with the database by way of a remote server, for example. This version has the advantage that the evaluation result signal is provided not only as a function of the value(s) of the physical parameter, but also (when desired) as a function of the manufacturing data characterizing the particular implant, and therefore the adaptation of the charging program is more specific.

If the evaluation unit is located at a large distance from the implant to be maintained, the evaluation unit preferably communicates with the control unit and the monitoring device by way of a wireless or wired data network, such as the internet.

The evaluation unit generates the evaluation result signal independently and automatically, or also as a function of manual input.

In another version, the evaluation unit is contained directly in the implant. In this version, the evaluation unit preferably receives data of other implants and/or data from the manufacturing database by way of the transceiver and generates the evaluation result signal as a function of the captured value(s) of the physical parameter and the additional data that is received.

In a further particularly preferred version of the maintenance system, the control unit is configured to control the charging device and the monitoring device such that periodic charging of the capacitor is carried out in accordance with the following charging procedure:
  initiating the charging of the capacitor by the charging device;
  capturing a voltage of the capacitor by means of the monitoring device;
  interrupting the charging process for a first defined time period after a first defined capacitor voltage of the capacitor has been reached;
  continuing the charging of the capacitor after expiration of the first time period;
  by means of the monitoring device, capturing the value of the physical parameter in the form of a second time period, which lasts from the start of charging continuation until the first charging voltage is reached again;
  sending the captured second time period to the evaluation unit by means of the transceiver;
  evaluating the second time period in the evaluation unit, which provides the evaluation result signal;
  receiving the evaluation result signal by means of the transceiver, and adapting the charging program as a function of the evaluation result signal by means of the control unit.

This version of the maintenance system reforms the energy accumulator arrangement of the maintenance system for the implant at periodic intervals (every three months, for example). The charging process of the capacitor is characterized in particular by a determined interruption of the charging process, which takes place when the first defined capacitor voltage is achieved, which is preferably below the rated voltage of the capacitor. While the charging process is interrupted for the duration of the first defined time period, self-discharging of the capacitor causes the capacitor voltage to decrease. After the first defined time period has expired, the charging device continues the charging process. During this charging of the capacitor, the first defined capacitor voltage is again achieved, specifically after expiration of the second time period. The duration of this second time period is dependent on the properties of the capacitor, battery, and charging device. The monitoring device captures the duration of the second time period as a value of the physical parameter and transmits the value to the evaluation unit using the transceiver. The evaluation unit preferably receives several values for this time period from several energy accumulator arrangements of different implants, the arrangements having identical designs. The evaluation unit evaluates at least one of these values—and preferably several of these values—and generates the evaluation result signal as a function of the evaluation. After transmitting the evaluation result signal, the control unit of the maintenance system adapts the charging program as a function of the evaluation result signal, preferably by changing the first defined capacitor voltage.

The several values of the second time period can be evaluated by the evaluation unit, which may then generate an evaluation result signal, after which the control unit changes the charging program, e.g., by shortening the reformation interval when a certain number of values of the second time period exceeds a specified value. For example, the control unit can adapt the charging program such that a reformation of the capacitor is carried out every 30 days using a reduced first defined capacitor voltage. In this way, premature destruction of the capacitor can be avoided.

In addition, the control unit preferably adapts the charging program in that a reformation process is aborted if the first defined capacitor voltage is not reached within a specified maximum time. In this case, the charging device can repeat a reformation in accordance with the charging program using a reduced capacitor voltage until complete reformation is possible.

Upon receiving the evaluation result signal, the control unit of the maintenance system is preferably configured to adapt the charging program by reducing the value of the first defined charging voltage if the evaluation result signal indicates that the second time period has exceeded a specified time duration.

Furthermore, after lowering the first defined charging voltage and again exceeding the specified time duration, the control unit is preferably configured to again lower the value of the lowered first defined charging voltage until the second time period no longer exceeds the specified time duration.

Reforming the capacitor according to the charging program described above is particularly gentle for the capacitor, so that the capacitor (and therefore the implant) achieve a long service life. In addition, damage to the capacitor is avoided.

In all versions of the maintenance system, the evaluation unit is preferably configured to evaluate not only a single value of the physical parameter, but several values of the physical parameter, which preferably originate with several different implants of energy accumulator arrangements having identical designs. In this way, as described above, a more informed evaluation can be carried out, and the control unit in this way can better adapt the charging program with respect to the advantageous effects mentioned above.

The monitoring device is preferably configured to capture a physical parameter in the form of a curve of a value of battery voltage present at the battery during a charging process of the capacitor. The control unit is then preferably configured to adapt the charging program for an evaluation result signal which is indicative of a need for maintenance on the basis of the captured battery voltage curve.

By capturing the battery voltage curve by means of the monitoring device during the charging process of the capacitor, the evaluation unit can detect a need for reforming the energy accumulator arrangement through a suitable evaluation of the curve. For example, a voltage delay can serve as an indication of the need for reformation. A voltage delay is caused by the formation of relatively high impedance layers on the battery anodes and thereby represents an increase in the internal resistance of the battery. This effect can only be detected when a relatively high voltage is to be withdrawn from the battery and the battery voltage drops disproportionately. A current load decreases these high impedance layers, thereby reducing or eliminating the voltage delay. In the case of a pronounced voltage delay, the evaluation unit generates an evaluation result signal after the control unit has adapted the charging program for the charging device such that the reformation intervals are shortened and repeat battery reformation is carried out incrementally at reduced charging voltages.

It is noted that for purposes of this document, a battery voltage shall denote a voltage which is present at the output terminals of the battery; a capacitor voltage shall denote a voltage present at the contacts of the capacitors; and a charging voltage shall denote a voltage of the charging device, with which the charging device charges the capacitor. The levels of the battery voltage, charging voltage, and capacitor voltage can of course deviate from each other at any time. The battery voltage is usually present in the same range as the charging voltage, and the capacitor voltage is considerably higher than the battery voltage.

In the version mentioned above, the control unit is preferably configured to adapt the charging program such that the charging device charges the capacitor in several consecutive charge cycles using a reduced charging voltage, and aborts one of the charge cycles if the value of the capacitor voltage does not reach a predetermined threshold value in a predetermined time period.

This version has the advantage that, with a moderate battery load, the oxide layers between the electrodes of the capacitor, which produce the voltage delay, can be systematically reformed.

In a further preferred version of the maintenance system, the control unit is configured to adapt the charging program, upon receiving the evaluation result signal, such that the charging device continuously charges the capacitor to a voltage level which is significantly below a rated capacitor voltage, then charges it incrementally until the rated capacitor voltage has been reached, and finally maintains the rated capacitor voltage by way of cyclical recharging if the evaluation result signal is indicative of increased leakage current of the capacitor.

This version of the maintenance system also achieves a longer service life of the energy accumulator arrangement, and therefore a longer service life of the implant. The incremental charging of the capacitor gently reforms the capacitor in that existing imperfections in the oxide layer can initially heal at a lower voltage, without resulting in supercritical local heating due to the leakage currents.

BRIEF DESCRIPTION OF THE DRAWINGS

Further advantages and features of the invention will be described below with reference to the figures, which show the following schematic illustrations.

DETAILED DESCRIPTION OF PREFERRED VERSIONS OF THE INVENTION

Figure 1:
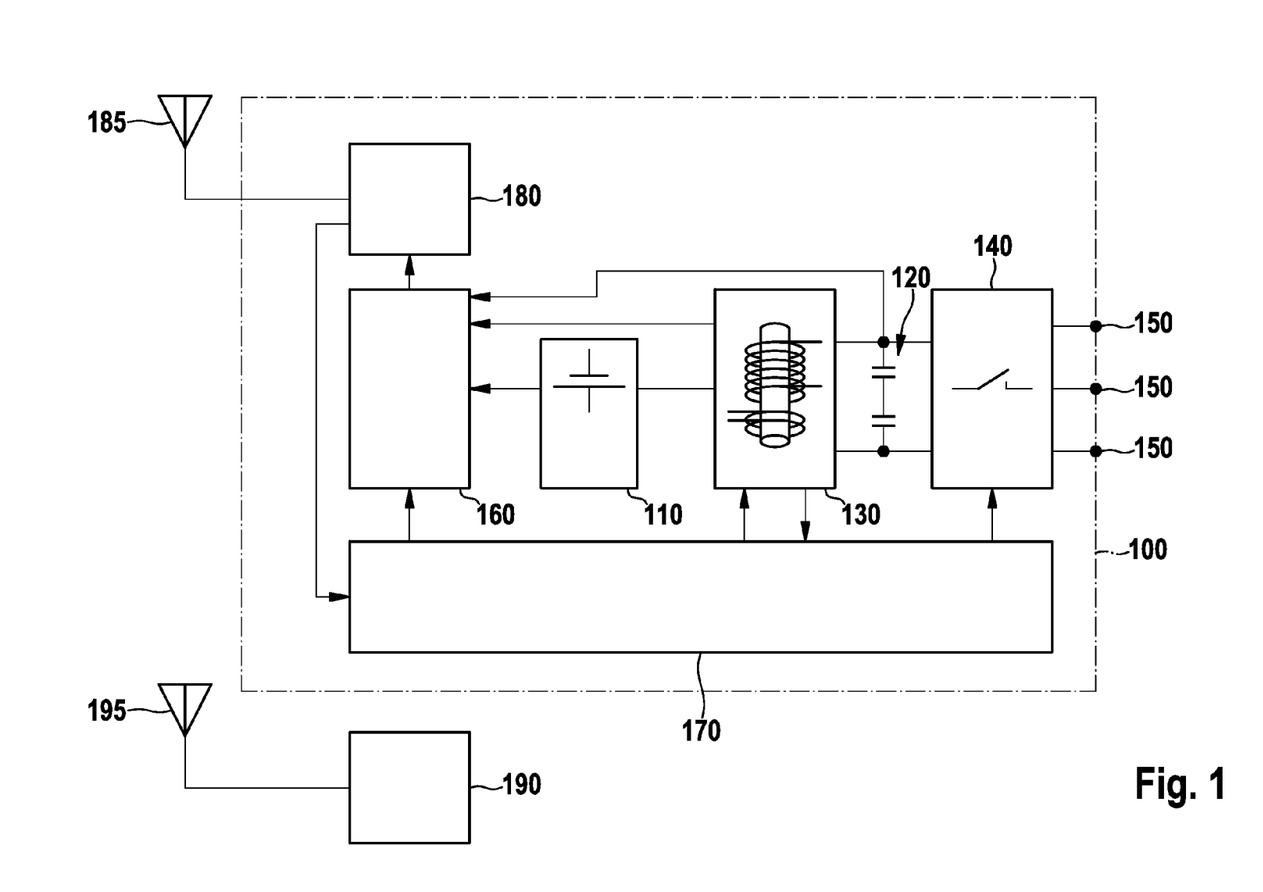
FIG. 1: Components of an exemplary version of the maintenance system.

FIG. 1 shows a schematic illustration of components of one version of the maintenance system. The maintenance system of FIG. 1 is used to maintain an energy accumulator arrangement 110, 120, 130 of an implant 100, including a battery 110 and a capacitor 120 connected to each other by a charging device 130. Connected downstream of the capacitor 120 is a circuit arrangement 140, by which capacitor energy of the capacitor 120 can be delivered to shock electrodes 150 of the implant 100. The implant 100 can be, for example, an implantable cardioverter/defibrillator.

The components of the maintenance system described in more detail below are primarily used to operate the charging device 130 so that a long service life of the battery 110 and capacitor 120 can be achieved by the charging device 130.

The maintenance system shown in FIG. 1 includes a monitoring device 160 contained in the implant 100 and configured to capture and provide a value of a physical parameter of the energy accumulator arrangement 110, 120, 130. The monitoring device 160 can be, for example, a measuring device for capturing a time duration, a voltage of the battery 110 (battery voltage), a voltage of the capacitor 120 (capacitor voltage), a current flowing in the charging device 13 (charging current), and/or an applied voltage (charging voltage).

The monitoring device 160, the charging device 130, and the circuit arrangement 140 are controlled by a control unit 170. A charging program is stored in the control unit 170, according to which the charging device 130 conducts the charge from the battery 110 to the capacitor 120.

The maintenance system illustrated in FIG. 1 furthermore includes a transceiver 180. The transceiver 180 is designed to send the value of the physical parameter captured by the monitoring device 160 to an evaluation unit 190. In the version of the maintenance system illustrated in FIG. 1, the evaluation unit 190 is located outside of the implant 100. Data is transmitted between the evaluation unit 190 and the implant 100, for example, by way of a patient device, which is not shown in detail in FIG. 1, and a wireless or wired network. The reference numerals 185 and 195 denote the necessary interfaces of the transceiver 180 and the evaluation unit 190, respectively. These operate, for example, in the GSM (Global System for Mobile Communications) or MICS (Medical Implant Communications Service) band.

The evaluation unit 190 is designed to generate an evaluation result signal as a function of the captured value of the physical parameter and to send it to the implant 100. The transceiver 180 receives the generated evaluation result signal and transmits it to the control unit 170. The control unit 170 is designed to adapt the charging program as a function of the evaluation result signal, according to which the charging device 130 charges the capacitor 120. The evaluation result signal of the evaluation unit 190 may also directly contain the reformation parameters.

Because the control unit 170 also controls the monitoring device 160, the value of the physical parameter, such as the battery voltage, the charging current, and/or the capacitor voltage, can be captured at certain points in time.

Figure 2:
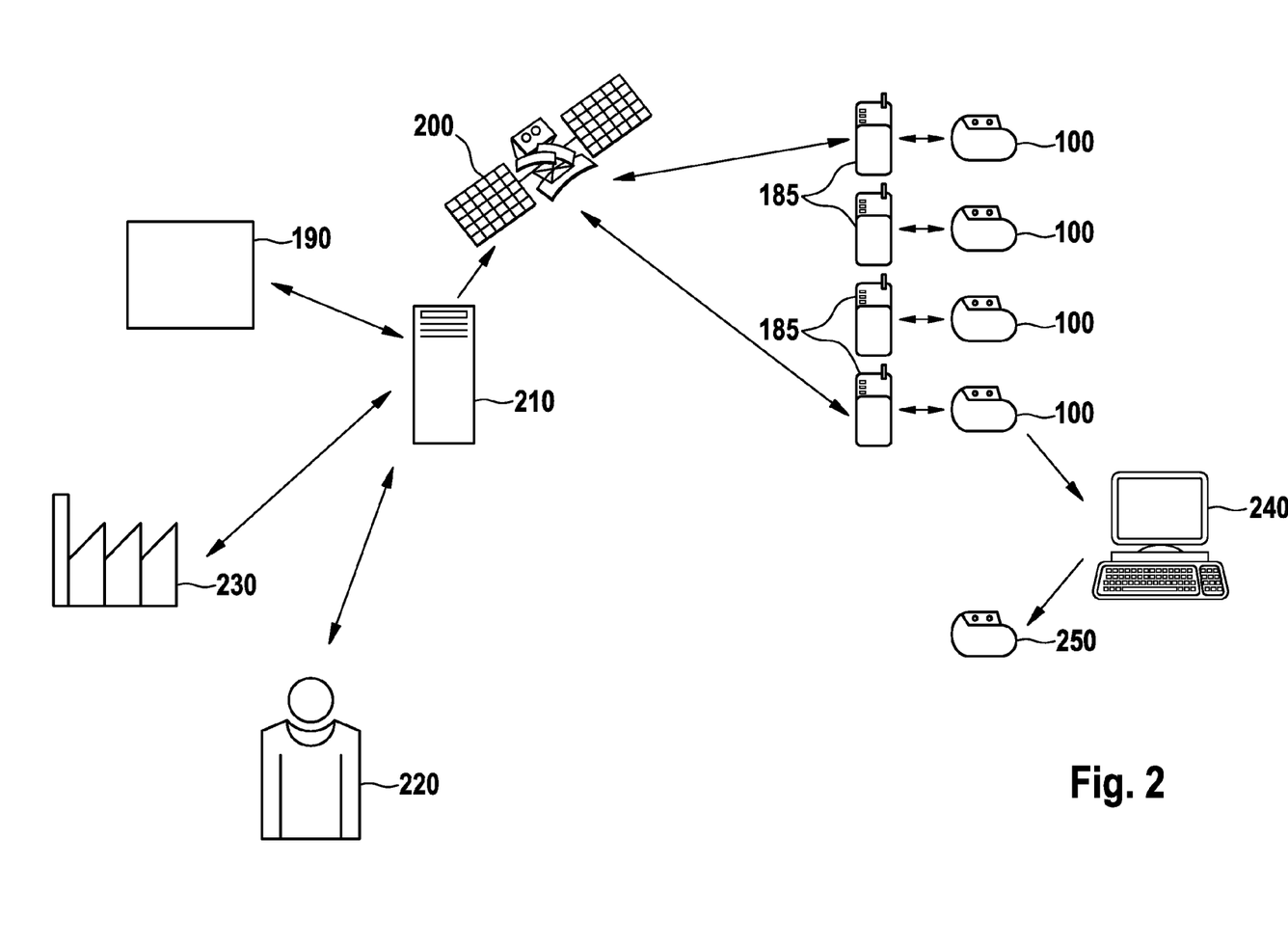
FIG. 2: an exemplary system for remotely managing several energy accumulator arrangements of different implants.

FIG. 2 is a schematic illustration of an overall system for remotely managing several energy accumulator arrangements of different implants 100, which have identical designs. The design of each implant 100 might substantially correspond to the design drawn schematically in FIG. 1. The implants 100 are connected to a data network 200 by way of interfaces 185, which are accommodated in a patient device, for example. The evaluation unit 190 of the maintenance system is connected to the same data network 200 by way of a remote monitoring server 210.

In this version, the evaluation unit 190 is designed to receive several values of the physical parameter of the energy accumulator arrangements of the several different implants 100 and to generate the evaluation result signal as part of an overall evaluation of these several values.

In addition, the overall system illustrated in FIG. 2 is designed such that a person 220 can influence the evaluation of the several values of the physical parameter in the evaluation unit 190 by way of the remote monitoring server 210, and can thereby influence the adaptation of the charging program. Furthermore, the evaluation unit 190 can access a database 230 including manufacturing data characterizing the several implants 100 by way of the remote monitoring server 210. In this way, the charging program can be adapted more specifically.

The overall system illustrated in FIG. 2 is designed, for example, such that values of several physical parameters of the batteries and/or capacitors of the energy accumulator arrangements of the implants 100 are collected, and the evaluation unit 190 continuously and automatically analyzes them, wherein the collected data can be supplemented with information from the database 230. Additionally, a person 220 can manually influence the evaluation of the data and can therefore directly influence the pattern of the charging program.

If one of the implants 250 does not have a connection to the data network 200, it is possible to read the adapted charging program of an implant 100 which is connected to the data network 200 using a programming device 240 and to then transmit it to the implant 250 which is not connected to the data network 200.

Figure 3:
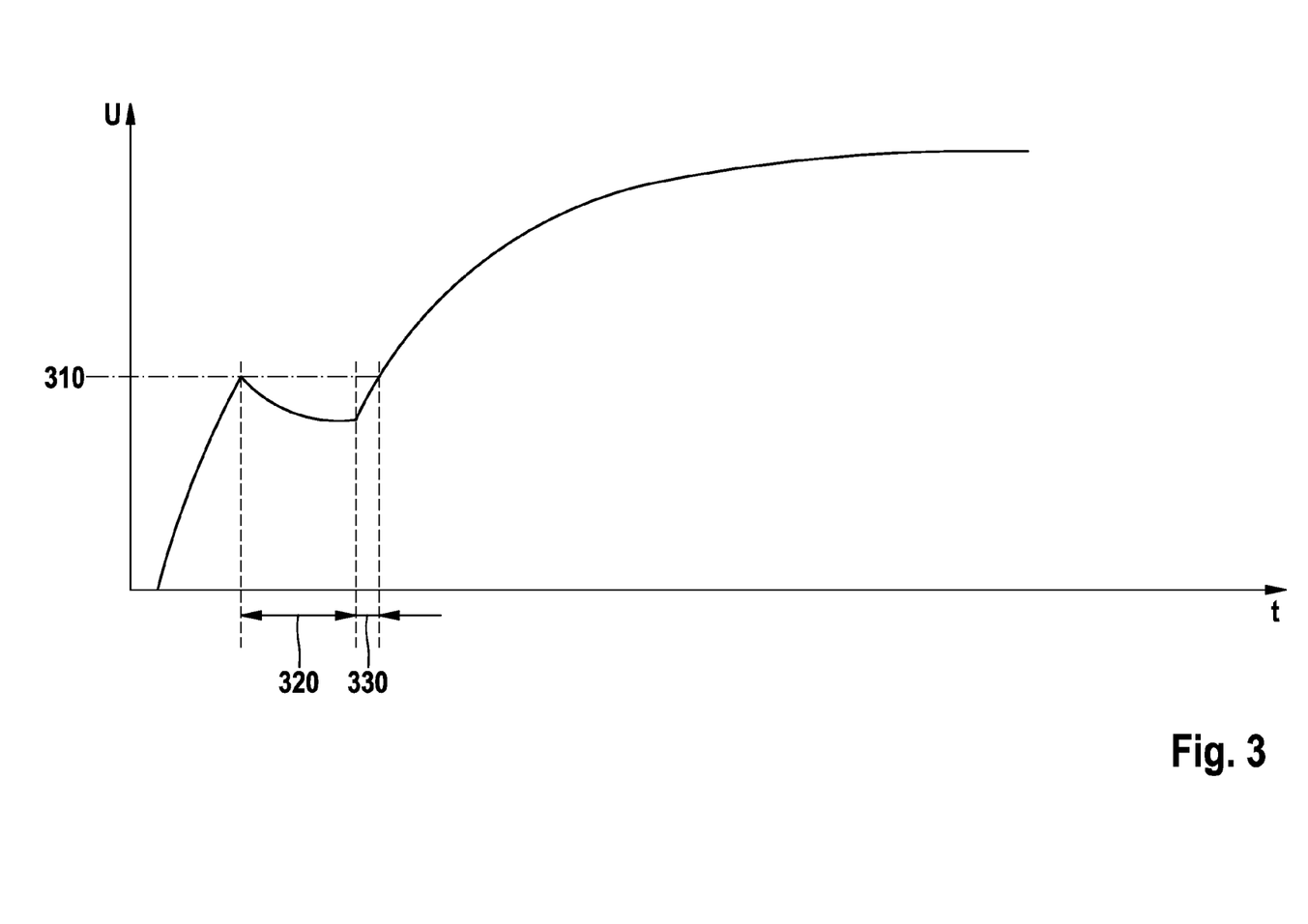
FIG. 3: a first curve of a capacitor voltage during charging of the capacitor in accordance with an exemplary charging program.

FIG. 3 shows a schematic illustration of a first curve of the capacitor 120 during charging according to a charging program. The charging device 130 charges the capacitor 120 up to a first defined capacitor voltage 310. Thereafter, the charging device 130 interrupts the charging process for the duration of a first defined time period 320. During this time period 320, the voltage of the capacitor 120 decreases due to self-discharge. After the first time period 320 has expired, the charging device 130 continues the charging process. The monitoring device 160 captures the time 330 it takes to charge the capacitor up until the first defined capacitor voltage 310 is reached again. The monitoring device 160 captures the duration of this second time period 330 and uses the transceiver 180 to send this information to the evaluation unit 190. The second time period 330 is a measure of the self-discharge of the capacitor 120.

Figure 4:
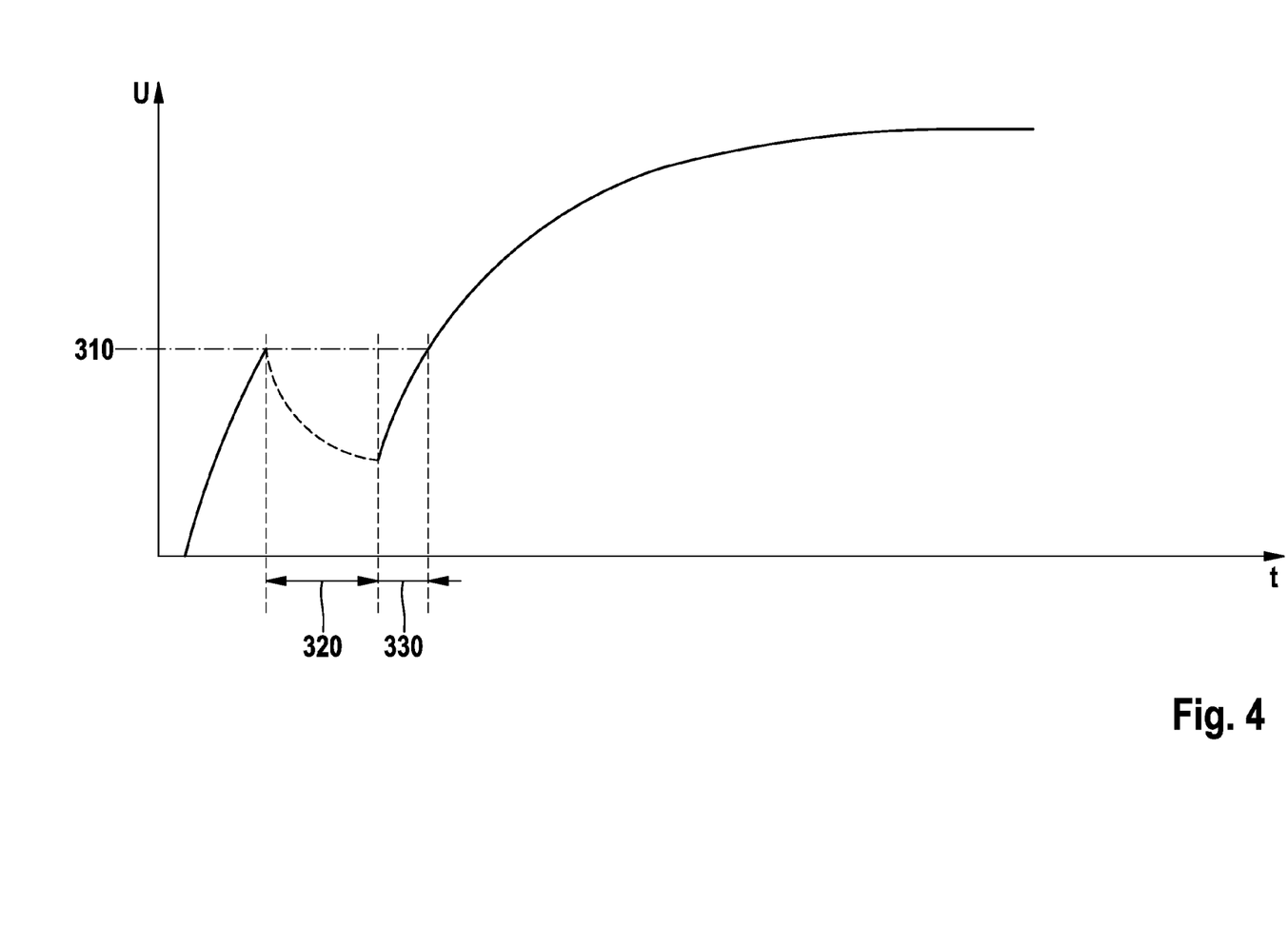
FIG. 4: a second curve of a capacitor voltage during charging of the capacitor in accordance with the exemplary charging program of FIG. 3.

When the second time period 330 exceeds a specified time duration, which is shown in FIG. 4, it is an indication of excessive self-discharge of the capacitor 120. If this is the case, the control unit 170 adapts the charging program by lowering the value of the first defined capacitor voltage 310 to a reduced capacitor voltage 340. This case is shown schematically in FIG. 5.

Figure 5:
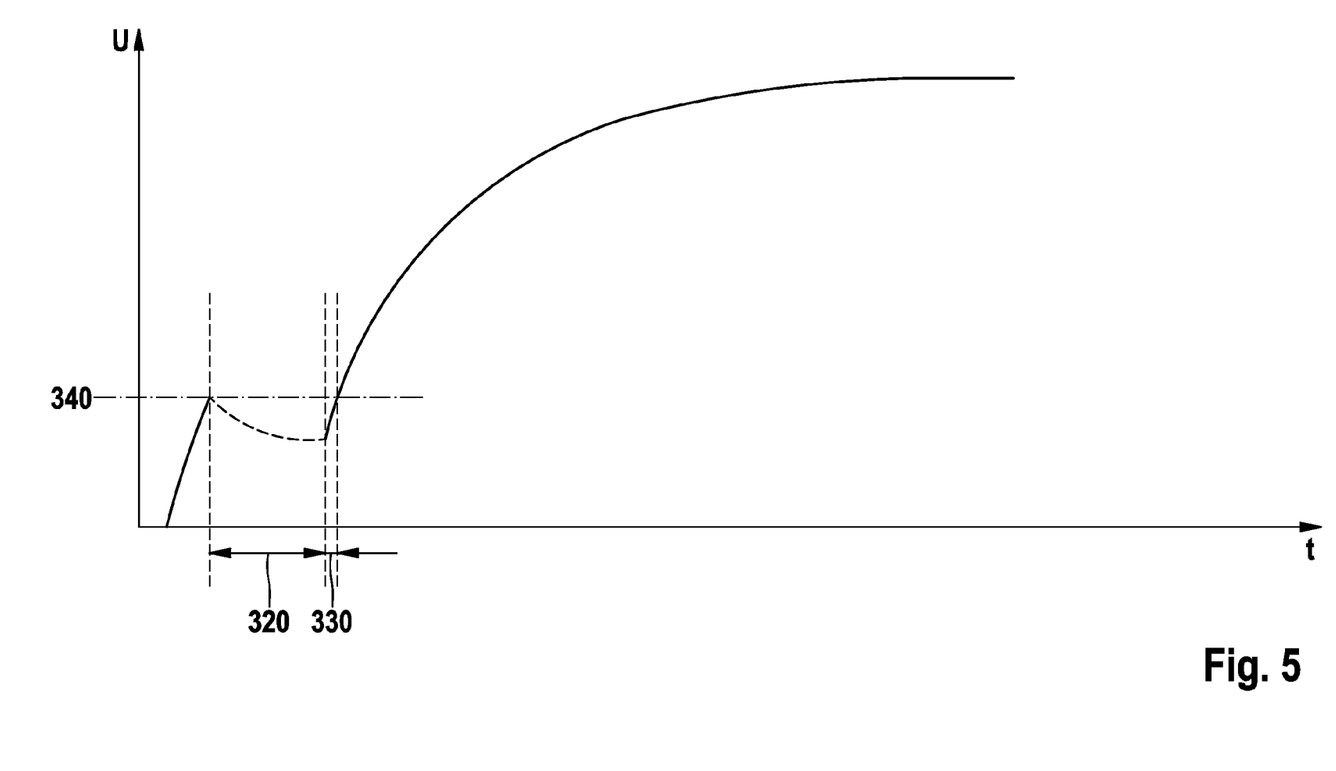
FIG. 5: a third curve of a capacitor voltage during charging of the capacitor in accordance with the exemplary charging program of FIGS. 3-4.

Charging the capacitor 120 according to FIGS. 3 to 5 reforms the capacitor 120 particularly gently. The charging program is preferably adapted within the scope of the overall system illustrated in FIG. 2.

Figure 8:
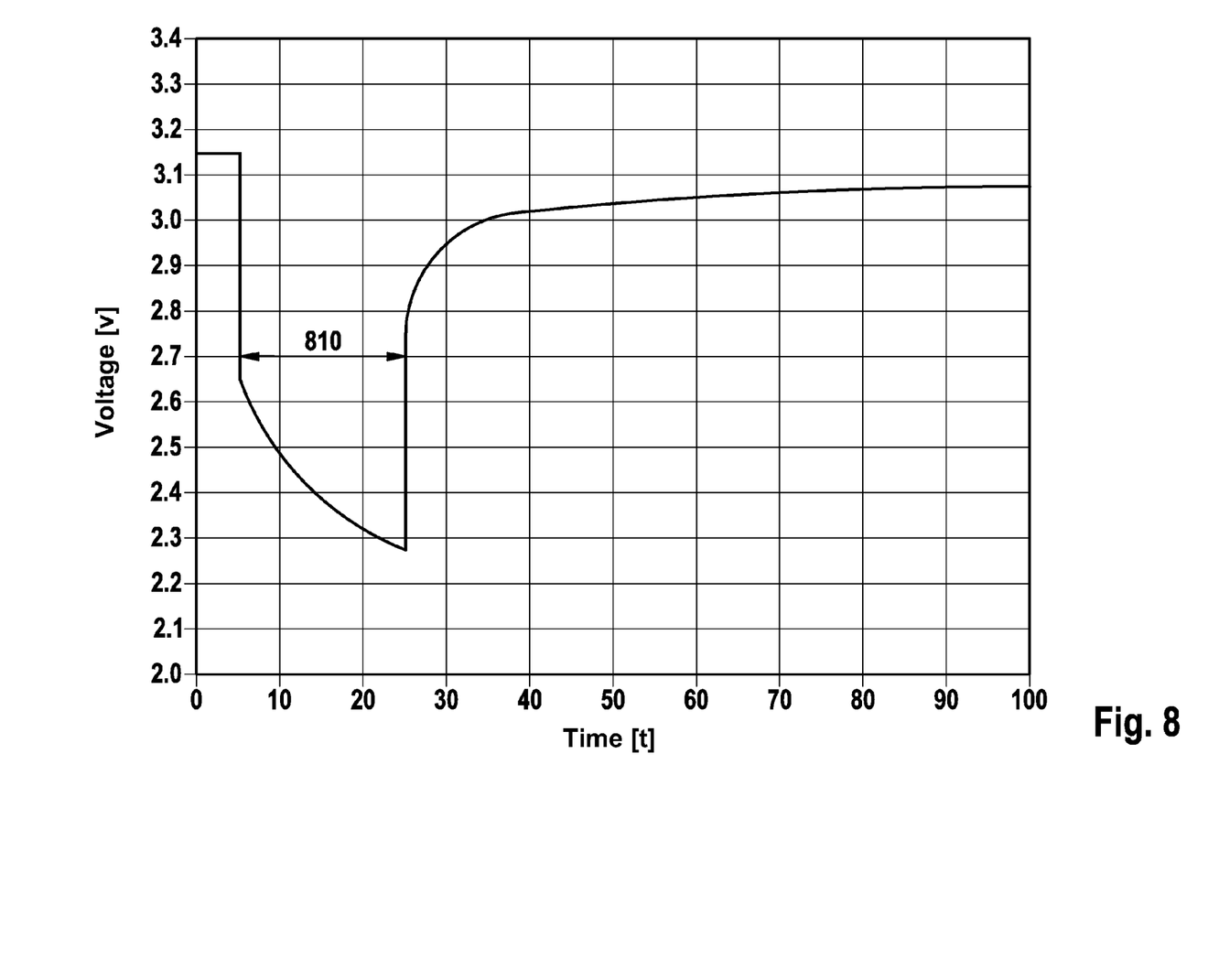
FIG. 8: an exemplary first curve of a battery voltage during charging of the capacitor, wherein the battery has increased leakage current.

Charging the capacitor 120 in accordance with FIGS. 3 to 5 is also advantageous if the capacitor 120 has increased leakage current. In order to detect the increased leakage current, the monitoring device 160 captures the voltage of the battery 110 while the capacitor 120 is being charged. If the battery voltage has a curve resembling that illustrated in FIG. 8, a noticeably long charging time 810 is indicative of a capacitor 120 having increased leakage current.

Figure 7:
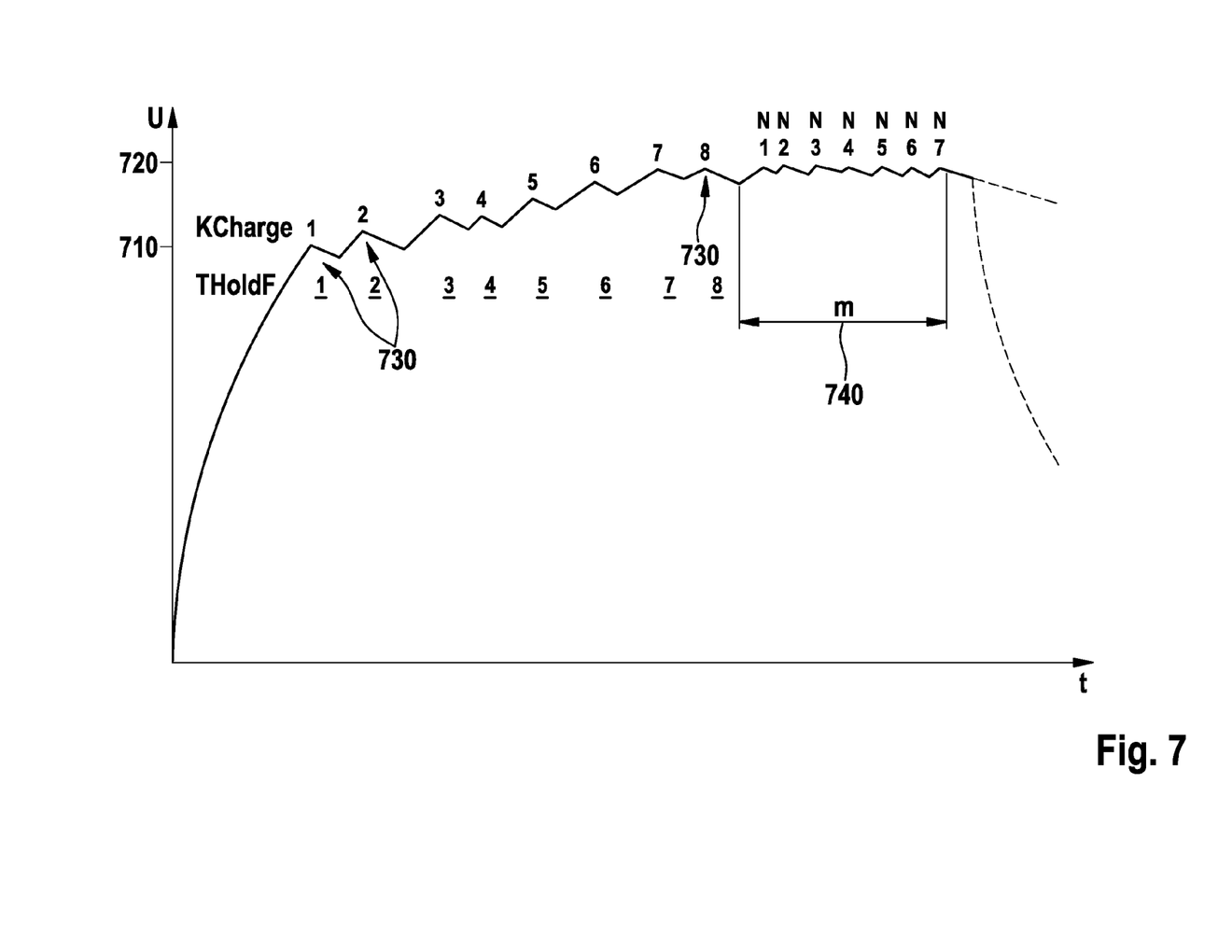
FIG. 7: a fifth curve of a capacitor voltage during charging of the capacitor in accordance with an exemplary charging program.

As an alternative to the curves illustrated in FIG. 3 to FIG. 5, a capacitor having increased leakage current can also be reformed according to a charge curve from FIG. 7. To this end, the charging device 130 initially continuously charges the capacitor 120 up to a voltage level 710 which is considerably below the rated capacitor voltage. Then, the charging device 130 charges the capacitor 120 incrementally (730) until the rated capacitor voltage 720 has been reached. The charging device 130 maintains the rated capacitor voltage 720 through cyclical recharging 740. The parameters for a reformation according to FIG. 7 are highly dependent on the respective defect of the capacitor 120 and are preferably set by the evaluation unit 190.

Figure 9:
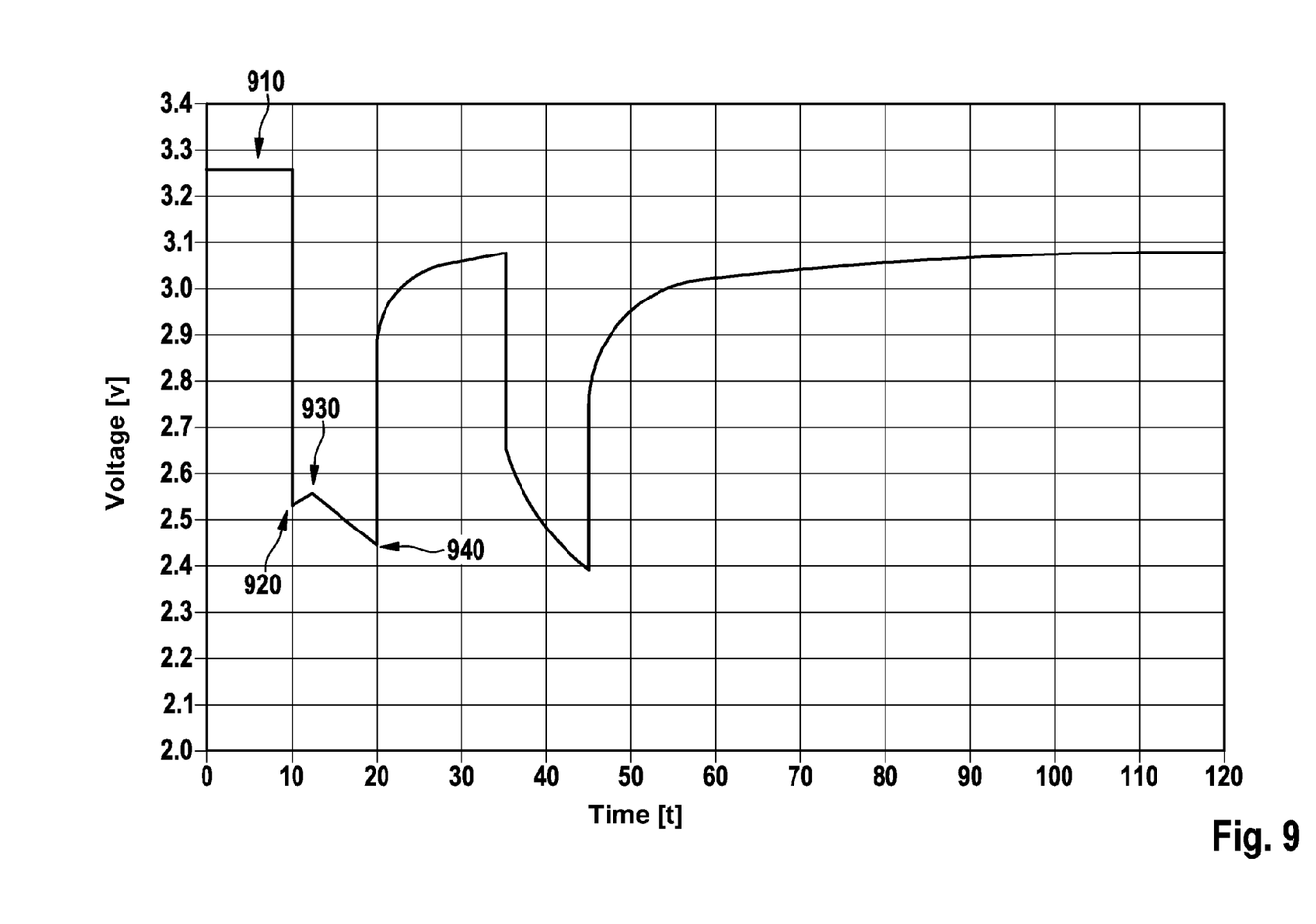
FIG. 9: an exemplary second curve of a battery voltage during charging of a capacitor, wherein the battery exhibits a minor voltage delay.
Figure 10:
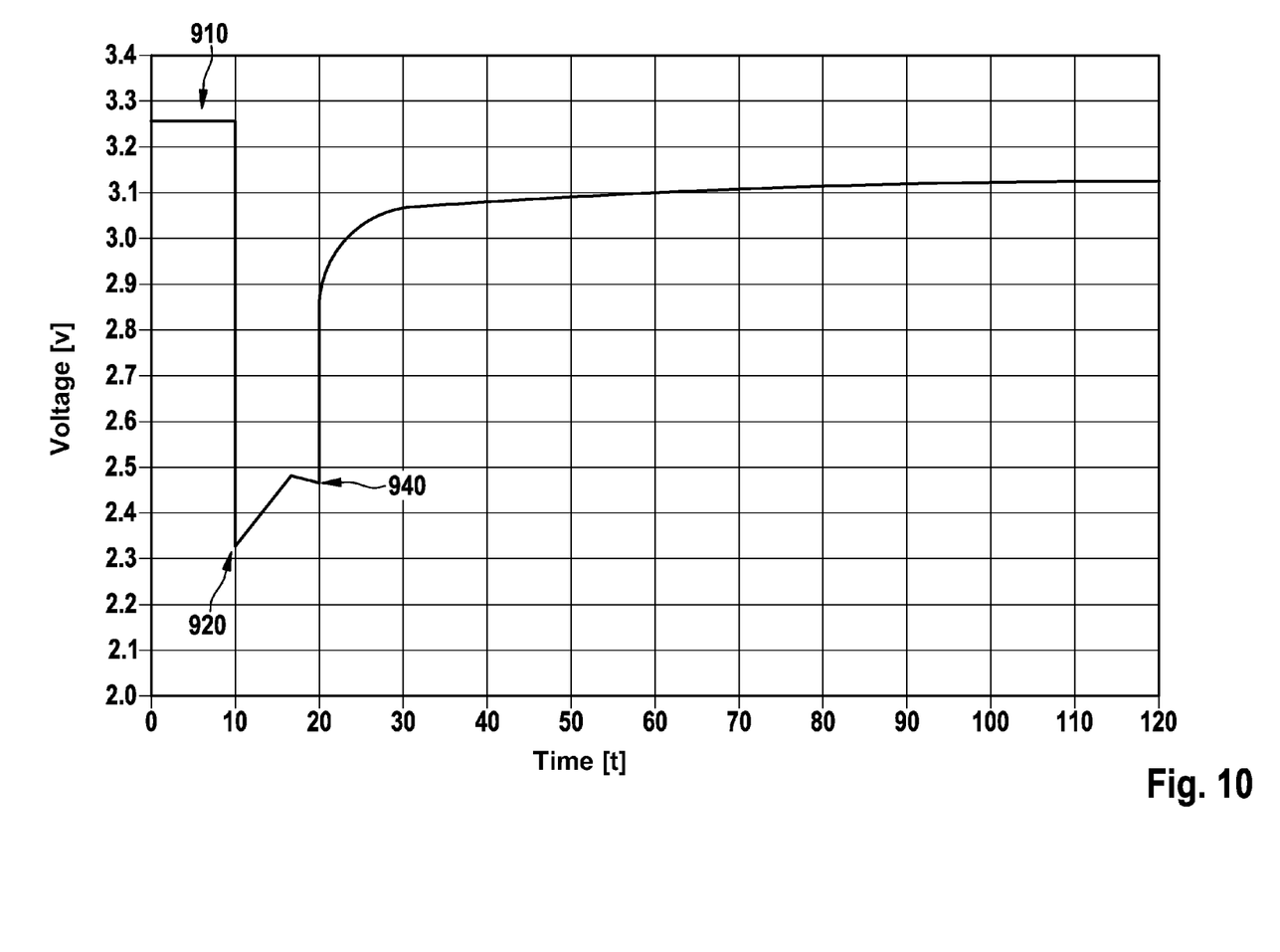
FIG. 10: an exemplary third curve of a voltage of a battery during charging of a capacitor, wherein the battery exhibits a major voltage delay.

FIGS. 9 and 10 show the voltage curves of the battery 110 over time during charging of the capacitor 120. The monitoring device 160 is designed to capture such voltage curves. FIG. 9 illustrates the battery voltage curve of two consecutive charging processes. As the charging process starts, an open-circuit voltage 910 of the battery 110 drops to an initial value 920 due to a voltage decline on an internal resistance of the battery 110 and due to electrochemical processes. During the first charging process, a slight initial voltage increase 930 takes place due to chemical processes inside the battery 110. This voltage increase 930 is an indication of a minor voltage delay. In this case, an end-point voltage 940 is considerably below the initial value 920.

During the second charging process, the battery 110 exhibits a normal voltage curve with a steady decrease of the battery voltage while a battery load is applied, this being during charging of the capacitor 120. In order to counteract a minor voltage delay, the control unit 170 adapts the charging program by shortening the reformation intervals.

FIG. 10 illustrates a curve of the voltage of the battery 110 captured by the monitoring device 160, wherein the battery 110 has a pronounced voltage delay. Starting from the usual open-circuit voltage 910 of the battery, the voltage drops to an unusually low initial value 920 as the charging process starts, and then rises during charging of the capacitor 120. In this case, the end-point value 940 of the battery voltage is clearly above the initial value 920. A voltage curve as shown in FIG. 10 is a clear indication of a pronounced voltage delay and therefore points to a drastically increased need for reformation.

Figure 6:
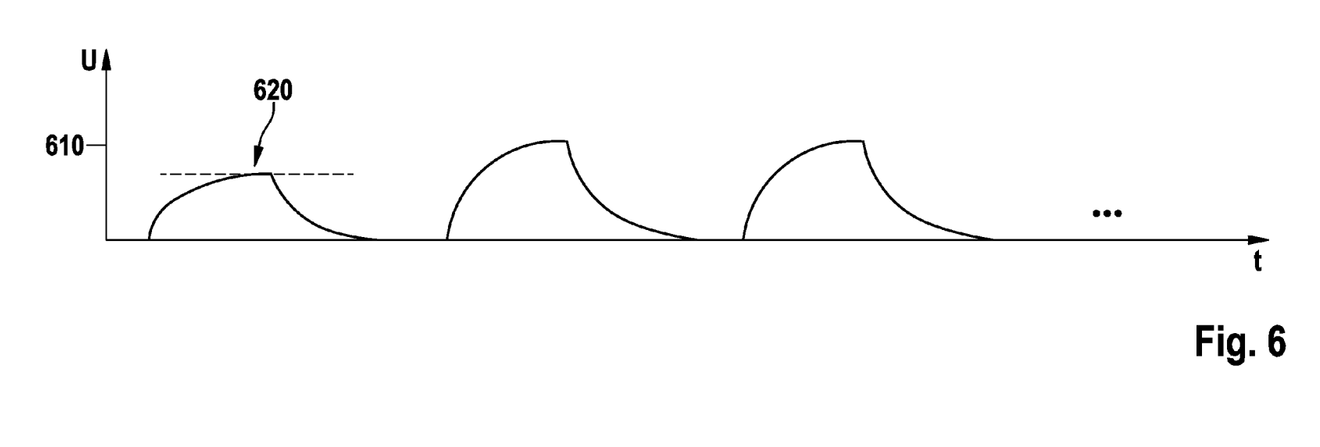
FIG. 6: a fourth curve of a capacitor voltage during charging of the capacitor in accordance with an exemplary charging program suitable for use when a battery has a significant voltage delay, as in FIG. 10.

Upon detecting a pronounced voltage delay, the evaluation unit 190 causes the charging program to be adapted, thereby resulting in a curve of the capacitor voltage exemplified by FIG. 6. The control unit 170 adapts the charging program such that the charging device 130 charges the capacitor 120 in several consecutive charge cycles using a reduced charge voltage, and aborts one of the charge cycles if the value of the capacitor voltage does not reach a predetermined threshold value 610 in a predetermined time period (as exemplified by the charging cycle 620).

This charging program has the advantage that an oxide layer resulting in the voltage delay can be systematically reformed with a moderate battery load.

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. A maintenance system for maintaining an energy accumulator arrangement of an implant, the energy accumulator arrangement including a battery, a capacitor, and a charging device configured to supply an electric charge from the battery to the capacitor in accordance with a charging program, wherein the maintenance system includes:
    a. a monitoring device contained in the implant, the monitoring device being configured to capture a physical parameter value of the energy accumulator arrangement;
    b. an evaluation unit configured to:
        (1) evaluate the captured physical parameter value, and
        (2) generate an evaluation result signal as a function of the captured physical parameter value;
    c. a transceiver contained in the implant, the transceiver being configured to:
        (1) send the captured physical parameter value to the evaluation unit, and
        (2) receive the evaluation result signal generated by the evaluation unit; and
    d. a control unit contained in the implant, the control unit being configured to:
        (1) control the charging device and the monitoring device to periodically charge the capacitor by:
            (a) initiating the charging of the capacitor by the charging device;
            (b) interrupting the charging process for a first defined time period after a first defined capacitor voltage of the capacitor has been reached;
            (c) continuing the charging of the capacitor after expiration of the first time period;
            (d) capturing the physical parameter value in the form of a second time period which at least approximates the time period between:
                i. the start of continued charging, and
                ii. the time when the first defined capacitor voltage is reached again;
            (e) sending the value of the captured second time period to the evaluation unit using the transceiver;
            (f) receiving the evaluation result generated by the evaluation unit as a function of the captured second time period, and
        (2) adapt the charging program as a function of the evaluation result signal.

2. The maintenance system of claim 1 wherein the evaluation unit is configured to:
    a. receive several captured physical parameter values of energy accumulator arrangements of several different implants, and
    b. generate the evaluation result signal as a function of the several captured physical parameter values.

3. The maintenance system of claim 1 further including a patient device separate and spaced from the implant, wherein the patient device is configured to:
    a. receive the captured physical parameter value from the transceiver and relay the captured physical parameter value to the evaluation unit, and
    b. receive the evaluation result signal generated by the evaluation unit and relay the evaluation result signal to the transceiver.

4. The maintenance system of claim 1 wherein the control unit is configured to adapt the charging program as a function of the evaluation result signal by changing one or more of:
    a. a charging voltage,
    b. a charging current, and
    c. a charging interval.

5. The maintenance system of claim 1 wherein the evaluation unit is configured to also generate the evaluation result signal as a function of manufacturing data characterizing the implant.

6. The maintenance system of claim 1 wherein the evaluation unit is contained in the implant.

7. The maintenance system of claim 1 wherein the control unit is configured to adapt the charging program by reducing the first defined capacitor voltage if the second time period has exceeded a specified time duration.

8. The maintenance system of claim 7 wherein the control unit is configured to lower the reduced first defined capacitor voltage until the second time duration no longer exceeds the specified time duration if, after lowering the first defined capacitor voltage, the specified time duration is again exceeded.

9. The maintenance system of claim 1 wherein:
    a. the monitoring device is configured to capture the physical parameter value in the form of a curve of a value of battery voltage present at the battery during a charging process of the capacitor, and
    b. the control unit is configured to adapt the charging program as a function of the evaluation result signal, wherein the evaluation result signal is indicative of a need for maintenance of the battery based on the battery voltage value curve.

10. The maintenance system of claim 9 wherein the control unit is configured to adapt the charging program such that the charging device:
    a. charges the capacitor in several consecutive charge cycles using a reduced charge voltage, and
    b. aborts one of the several charge cycles if the value of the capacitor voltage does not reach a predetermined threshold value in a predetermined time period.

11. The maintenance system of claim 1 wherein the control unit is configured to adapt the charging program such that the charging device:
    a. continuously charges the capacitor to a voltage level which is significantly below a rated capacitor voltage;
    b. subsequently charges the capacitor incrementally until the rated capacitor voltage has been reached; and
    c. thereafter maintains the rated capacitor voltage by cyclical recharging if the evaluation result signal is indicative of increased leakage current of the capacitor.

12. A method for maintaining an energy accumulator of an implant wherein the energy accumulator includes a battery, a capacitor, and a charging device configured to supply an electric charge from the battery to the capacitor in accordance with a charging program, the method including:

a. using the charging device to charge the capacitor in accordance with the charging program;

b. interrupting the charging or the capacitor for a first defined time period after a first defined capacitor voltage has been reached;

c. continuing the charging of the capacitor after expiration of the first time period;

d. capturing a physical parameter value of the energy accumulator arrangement using a monitoring device contained in the implant, the physical parameter value being captured in the form of a second time period which at least approximates the time period between:

(1) the start of continued charging, and (2) the time when the first defined capacitor voltage is reached again:

e. sending the captured second time period to an evaluation unit using a transceiver;

f. within the evaluation unit:

(1) evaluating the captured second time period, and (2) generating an evaluation result signal as a function of the captured second time period;

g. receiving the evaluation result signal generated by the evaluation unit using the transceiver; and h. adapting the charging program as a function of the evaluation result signal.

13. The maintenance system of claim 12 wherein the charging program is adapted by reducing the first defined capacitor voltage if the second time period exceeds a specified time duration.

14. The maintenance system of claim 13 wherein the reduced first defined capacitor voltage is lowered until the second time duration no longer exceeds the specified time duration if, after lowering the first defined capacitor voltage, the specified time duration is again exceeded.

15. The maintenance system of claim 12 further including the step of capturing the physical parameter value in the form of a curve of a value of battery voltage present at the battery during a charging process of the capacitor.

16. The maintenance system of claim 15 wherein the step of adapting the charging program includes:

a. charging the capacitor in several charge cycles using a reduced charge voltage, and b. aborting one of the several charge cycles if a capacitor voltage value does not reach a predetermined threshold value within a predetermined time period.

17. The maintenance system of claim 1 wherein the step of adapting the charging program includes:

a. continuously charging the capacitor to a voltage level which is significantly below a rated capacitor voltage;

b. subsequently charging the capacitor in incremental steps until the rated capacitor voltage has been reached; and c. thereafter maintaining the rated capacitor voltage by repeated recharging if the evaluation result signal is indicative of increased leakage current of the capacitor.

* * * * *